United States Patent [19]

Phillips

[11] Patent Number: 4,541,125
[45] Date of Patent: Sep. 17, 1985

[54] EYEGLASSES APPARATUS, AND METHODS OF CONSTRUCTING AND UTILIZING SAME

[76] Inventor: Robert J. Phillips, 27427 Schoenherr, Warren, Mich. 48093

[21] Appl. No.: 524,604

[22] Filed: Aug. 19, 1983

[51] Int. Cl.$^4$ ............................................. A42B 1/24
[52] U.S. Cl. ........................................... 2/10; 2/199; 2/453; 351/155
[58] Field of Search ................. 2/10, 199, 185 R, 453, 2/12; 351/155

[56] References Cited

U.S. PATENT DOCUMENTS 1,334,878  3/1920  Young ................................. 351/155
2,691,164  10/1954  Feldman ................................. 2/10

FOREIGN PATENT DOCUMENTS 0685696  11/1939  Fed. Rep. of Germany ............ 2/10
0476306  5/1915  France ................................. 2/10
1174669  11/1958  France ................................. 2/10
0459277  9/1950  Italy ................................. 2/453

*Primary Examiner*—Peter Nerbun
*Attorney, Agent, or Firm*—Irving M. Weiner; Pamela S. Burt

[57] ABSTRACT

An eyeglasses apparatus for attachment to a cap visor; the apparatus comprises two main parts, including a clip part which is selectively removably attachable to a cap visor and a main eyeglasses part which is hingedly engageable with a member of the clip part. The main eyeglasses part is integrally molded in a unitary construction, and preferably comprises either sunglasses or safety glasses. When the apparatus is attached to a cap visor, the main eyeglasses part can be readily pivotably moved between an operative position wherein the user's eyes are shielded and an inoperative position wherein the main eyeglasses part is disposed adjacent the underside of the cap visor.

6 Claims, 4 Drawing Figures

EYEGLASSES APPARATUS, AND METHODS OF CONSTRUCTING AND UTILIZING SAME

BACKGROUND OF THE INVENTION

1. Field of the Invention

The present invention relates generally to an eyeglasses apparatus. More particularly, the invention relates to an eyeglasses apparatus for attachment to the visor of a cap.

The terminology "eyeglasses" as employed herein is intended to connote, most particularly, sunglasses or safety glasses. The terminology "cap" as employed herein is intended to connote a cap or hat employed for sports activities, such as a baseball cap, a fisherman or boater's cap, etc., as well as other types of caps, such as safety caps to be worn for protective purposes in various types of work places.

2. Description of Relevant Art

In various types of sporting and working activities, some type of cap is often worn in conjunction with the use of, or need for, either sunglasses or safety glasses. Such is the case, for example, for baseball players, hunters, boaters, skiers, construction workers, etc.

Heretofore, a number of devices have been proposed for attaching eyeglasses to the visor of a cap. The following devices are illustrative.

U.S. Pat. No. 862,795 issued in 1907 to Blackiston discloses a device wherein a first part is permanently secured to a cap visor, and a detachable second part is supported by the first part. The second part supports a conventional pair of eyeglasses such that when a button provided above the cap visor is pressed, the eyeglass holder can be adjusted between a lowered operative position or a raised inoperative position.

U.S. Pat. No. 1,334,878 issued in 1920 to Young discloses a device for supporting eyeglasses from the visor of a cap. The device includes a swinging support arm hinged to a short arm projecting from a rigid frame attached to the visor cap, with the other end of the swinging arm being provided with a clamp for receiving the bridge-piece of a pair of conventional eyeglasses. The swinging arm permits swinging of the glasses between an operative and inoperative position, with a pair of spring clips being required for holding the swinging arm in an inoperative position.

U.S. Pat. No. 1,833,741 issued in 1931 to Diehl discloses an eye shield for attachment to a visor of a hat or cap. The glasses are formed of a transparent sheet such as celluloid. The attachment part of the device includes a pair of jaws which are pressed into gripping engagement with the glasses sheet, a crank shaft, and prongs which are passed through the visor and bent downwardly by a plate.

The above set forth illustrative known devices have various attendant disadvantages which have prevented them from meeting with widespread acceptance and use. For example, various ones of such devices require some type of modification to the visor itself, which may be highly undesirable if the user intends to employ the cap without the eyeglasses attachment. In addition, such devices are generally quite complex and require many component parts, while generally failing to afford the facility of use desired of such a device.

The present invention effectively overcomes the various disadvantages attendant the known devices, and at the same time provides an eyeglasses attachment for a cap visor which is simplified in construction, comprises only two main component parts, and may be easily and conveniently used.

SUMMARY OF THE INVENTION

The present invention provides an eyeglasses apparatus for attachment to the visor of a cap, the apparatus including a clip part and a main eyeglasses part. The clip part is adapted to be selectively removably attached to a cap visor, and includes a substantially elongated member extending substantially in the transverse direction of the visor. The main eyeglasses part includes integral means for clipping the main eyeglasses part onto the elongated member of the clip part, such clipping means extending integrally upwardly from a central portion of the main eyeglasses part. The clipping means is selectively directly engageable with the elongated member of the clip part so as to pivotably support the main eyeglasses part from the clip part such that the main eyeglasses part is pivotably movable between an operative position wherein the eyeglasses part shields the eyes of a user and an inoperative position wherein the main eyeglasses part extends substantially parallel with the cap visor.

In a preferred embodiment, the eyeglasses apparatus according to the invention includes only two main component parts, i.e., the clip part and the main eyeglasses part, with the clipping means of the main part being integrally molded in a unitary construction of the main part. The clipping means includes a plurality of fingers adapted to frictionally engage the elongated member of the clip part so as to securely retain the main eyeglasses part in either the operative or the inoperative position, while permitting pivotable movement of the main eyeglasses part between such positions. The invention thus eliminates any need for auxiliary positioning means, while ensuring that the eyeglasses part will be properly retained in the desired position.

The clip part of the apparatus is readily and conveniently attachable to the visor of a cap merely by clipping two hooked end portions of the clip part onto side portions of the cap visor, thus avoiding any undesirable modification of the cap visor itself.

The above and further objects, details and advantages of the present invention will become apparent from the following detailed description, when read in conjunction with the accompanying drawings.

DETAILED DESCRIPTION OF PREFERRED EMBODIMENTS

Figure 1:
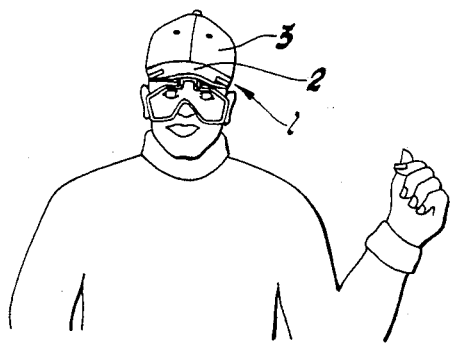
FIG. 1 is a front perspective view of the eyeglasses apparatus according to the invention as attached to the visor of a cap worn by a user, with the main eyeglasses part in an operative position.
Figure 2:
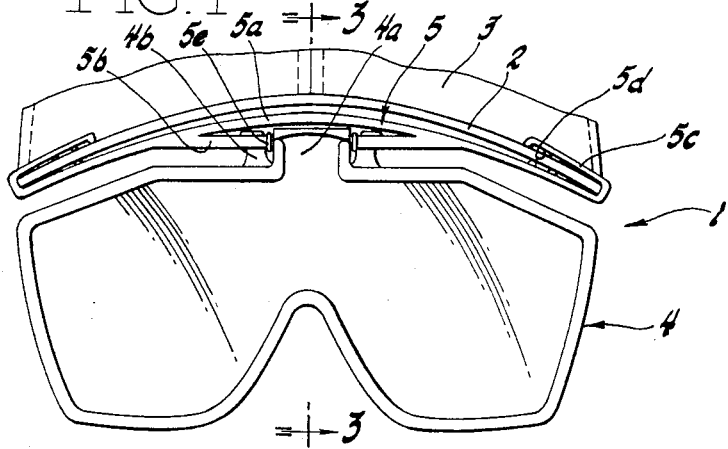
FIG. 2 is a front elevational view of the eyeglasses apparatus attached to a cap visor, with the main eyeglasses part in an operative position.
Figure 3:
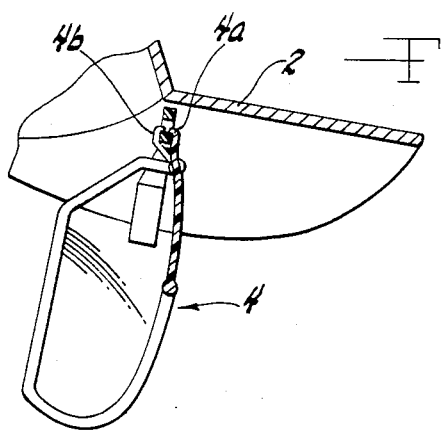
FIG. 3 is a side elevational view of the eyeglasses apparatus attached to a cap visor, with the main eyeglasses part in an operative position.
Figure 4:
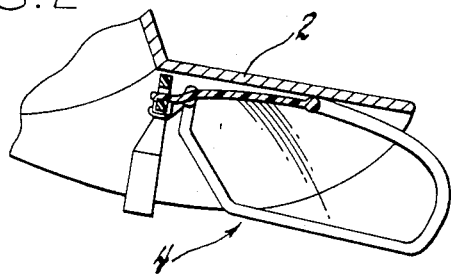
FIG. 4 is a side elevational view of the eyeglasses apparatus attached to a cap visor, with the main eyeglasses part in an inoperative position.

With reference to FIG. 1, there is shown an eyeglasses apparatus 1 in accordance with the present invention as attached to a visor 2 of a cap 3 worn by a user. The eyeglasses apparatus 1 is shown in FIGS. 1–3 with a main eyeglasses part 4 thereof disposed in an operative position wherein it will shield the eyes of a user. In FIG. 4, the main eyeglasses part 4 is shown in an inoperative position wherein it extends substantially parallel with the cap visor, closely below the underside surface of the visor 2.

The main eyeglasses part 4 of the apparatus according to the invention is integrally molded in a unitary construction from a substantially transparent material, such as plastic. It will be understood that such material may be colored as desired so as to provide a light-screening effect, in which case the main eyeglasses part 4 will serve as sunglasses. Such material may alternatively be uncolored, such as when the main eyeglasses part 4 is to serve as safety glasses. In either case, it will be understood that such material, particularly those portions forming the lens portions of the eyeglasses, may desirably be coated with a scratch-resistant material. Further, the main part 4 is formed to be optically clear, without distortions.

The unitary main eyeglasses part 4 is curved so as to substantially conform to the inner curved surface of a conventional cap visor, and thus when the main part 4 is pivoted to its inoperative position as shown in FIG. 4, it will be disposed substantially parallel with the cap visor 2 and close to the underside surface thereof. In such position, the main part 4 will be disposed well out of the user's ordinary field of vision. The main eyeglasses part 4 further includes a lower recessed nose-fitting portion, and has an overall shape similar to conventional eye shields, except that the conventional bridge piece is replaced by a unitary integrally-molded portion of the eyeglasses material.

Formed integrally with an upper central portion of the main eyeglasses part 4 is the clipping means in accordance with the invention. Such clipping means comprises a central finger 4a and a pair of side fingers 4b, the side fingers 4b being disposed on respective sides of the central finger 4a and extending in oppositely facing relation thereto; such fingers 4a, 4b being integrally molded with the main part 4 so as to extend upwardly from the central portion thereof.

The apparatus includes as its second major component a substantially rigid clip part 5. Clip part 5 is integrally molded from a suitable material, such as plastic, and includes an elongated curved member 5a and an elongated straight member 5b. The entire clip part 5, including members 5a and 5b, is adapted to extend transversely of the cap visor when attached thereto. The curved member 5a is curved so as to substantially conform to the curvature of a conventional cap visor 2, and extends closely along an underside surface of the visor 2 when the clip part 5 is attached to the visor. The curved member 5a may desirably have a substantially rectangular cross section in the central portion thereof, while the end portions are widened into a wedge-like shape for strengthening purposes, as shown in FIGS. 3 and 4. Both ends of curved member 5a are provided with an integral hooked end portion 5c having a substantially U-shaped cross section and being adapted to engage in a clip-on manner with respective side portions of the cap visor 2, as shown in FIG. 1. To ensure a more effective retention of the hooked end portions 5c on the sides of the visor 2, the inner surfaces of hooked end portions 5c are formed with a plurality of ridges or beads 5d which closely engage the material of the visor 2.

The straight member 5b of clip part 5 is integrally formed with the curved member 5a so as to extend across a central lower portion of curved member 5a and to define a circular segment opening together with the central lower portion of curved member 5a. Preferably, the straight member 5b has a substantially rectangular cross section. A pair of spaced-apart ridge portions 5e are formed around the periphery of straight member 5b so as to be equidistantly spaced from the center of member 5b, as shown in FIG. 1.

From the foregoing, it will be understood that the clip part 5 may be readily and conveniently attached to and detached from the visor 2 merely by selectively clipping-on or removing the hooked end portions 5d from the sides of the visor. Also, it is to be understood that the clip part and the main eyeglasses part may desirably be formed of the same material, such as plastic, while it is most desirable that a suitably lightweight material be selected in order that the overall weight of the apparatus is minimized.

The clipping means defined by the fingers 4a, 4b of the main eyeglasses part 4 are selectively directly hingedly engageable with the straight member 5b of the clip part 5 as follows. The clipping means of main part 4 are brought into alignment with straight member 5b of clip part 5, with the side fingers 4b aligned on one side of the straight member 5b such that they extend outwardly of the respective ridge portions 5e of straight member 5a, and the central finger 4a aligned on the opposite side of straight member 5b. The fingers 4a, 4b are then snapped into position such that opposing surfaces of straight member 5b are frictionally engaged by the side fingers 4b on the one hand and the central finger 4a on the other hand.

The straight member 5b of clip part 5 is closely frictionally engaged by the fingers 4a, 4b so as to securely retain the main eyeglasses part in either the operative position in which the user's eyes are shielded or the inoperative position in which the main part 4 rests closely adjacent the underside of visor 2, while still permitting pivotable movement of the main eyeglasses part 4 between such operative and inoperative positions. Any substantial lateral movement of the eyeglasses part 4 relative to clip part 5 is effectively prevented in both the operative and the inoperative positions by way of abutment of the side fingers 4b against the ridge portions 5a of straight member 5b, although it may be desirable to position the ridge portions 5a such that minor lateral movement of the main part 4 is permitted (e.g., ⅛ inch or less). Also, when desired, the main part 4 may be readily detached from clip part 5 merely by snapping the fingers 4a, 4b out of engagement with straight part 5b.

It is to be noted that in the operative position of main eyeglasses part 4, the side fingers 4b are disposed within the circular segment opening defined by curved member 5a and straight member 5b of clip part 5.

From the foregoing description it will be understood that the present invention provides a sunglasses/safety glasses apparatus which can be readily clipped or slid onto the visor of a cap of a baseball player, hunter, boater, skier, construction worker, or the like. When clipped in position on the visor 2, the eyeglasses part 4 can be readily flipped through an angle of 90° between the inoperative and operative positions, which is extremely convenient from the standpoint of a baseball player, for example, when a ball is coming to him from the sunlight. The two-piece construction of the invention permits ready attachment and detachment of the entire apparatus to and from the visor 2, as well as ready attachment and detachment of the two parts relative to each other. Further, the close frictional engagement between the fingers of the clipping means of main part 4 and the straight member 5b of clip part 5 eliminates any need for auxiliary means for retaining the eyeglasses part in the desired position, while still permitting pivotable movement between the operative and inoperative positions.

Although there have been described what are at present considered to be the preferred embodiments of the invention, it will be understood that the invention may be embodied in other specific forms without departing from the spirit or essential characteristics thereof. The present embodiments are therefore to be considered in all respects as illustrative, and not restrictive. The scope of the invention is indicated by the appended claims rather than by the foregoing description.

I claim:

1. An eyeglasses apparatus, comprising:
   a clip part adapted to be selectively removably attached to a cap visor;
   said clip part including a substantially elongated member extending substantially in the transverse direction of said cap visor when said clip part is attached thereto;
   a main eyeglasses part;
   means for clipping said main eyeglasses part onto said elongated member of said clip part;
   said clipping means being integrally formed with said main eyeglasses part so as to extend integrally upwardly from a central portion of said main eyeglasses part;
   said clipping means being selectively directly engageable with said elongated member of said clip part so as to pivotably support said main eyeglasses part from said clip part such that said main eyeglasses part is pivotably movable between an operative position wherein said main eyeglasses part shields the eyes of a user and an inoperative position wherein said main eyeglasses part extends substantially parallel with said cap visor;
   said clipping means comprising a plurality of upwardly extending fingers adapted to hingedly engage with said elongated member of said clip part;
   said elongated member of said clip part being substantially straight;
   said clipping means comprising a central finger and a pair of side fingers, said side fingers being disposed on respective sides of said central finger and extending in oppositely facing relation thereto;
   said clipping means being hingedly engageable with said elongated straight member of said clip part such that said central finger engages said straight member on a side thereof opposite to a side of said straight member engaged by said side fingers;
   said straight member of said clip part having a substantially rectangular cross section;
   a pair of spaced apart ridge portions being formed around the periphery of said straight member of said clip part;
   said side fingers engaging said straight member of said clip part adjacent respective ones of said spaced apart ridge portions; and
   said side fingers abutting said ridge portions so as to prevent lateral movement of said main eyeglasses part relative to said clip part.

2. An eyeglasses apparatus according to claim 1, wherein:
   said fingers of said clipping means frictionally engage said straight member of said clip part so as to securely retain said main eyeglasses part in either of said operative or inoperative positions, while permitting pivotable movement of said main eyeglasses part between said operative and inoperative positions.

3. An eyeglasses apparatus according to claim 2, wherein:
   said clip part further comprises an elongated curved member provided at both ends thereof with an integral hooked end portion having a substantially U-shaped cross section;
   said hooked end portions of said curved member being engageable in a clip-on manner with respective side portions of said cap visor;
   said curved member extending transversely along an underside portion of said cap visor when said hooked end portions are clipped on said cap visor; and
   said elongated straight member of said clip part being integrally formed with said curved member so as to extend across a central lower portion of said curved member and to define a circular segment opening together with said central lower portion of said curved member.

4. An eyeglasses apparatus according to claim 3, wherein:
   said side fingers of said clipping means are disposed within said circular segment opening while engaging a side of said straight member of said clip part when said main eyeglasses part is disposed in said operative position.

5. An eyeglasses apparatus according to claim 3, wherein:
   said hooked end portions of said curved member of said clip part are provided on the inner surfaces thereof with gripping ridges.

6. A combination cap and eyeglasses apparatus, comprising:
   a cap;
   a clip part adapted to be selectively removably attached to a visor of said cap;
   said clip part including a substantially elongated member extending substantially in the transverse direction of said cap visor when said clip part is attached thereto;
   a main eyeglasses part;
   means for clipping said main eyeglasses part onto to said elongated member of said clip part;
   said clipping means being integrally formed with said eyeglasses part so as to extend integrally upwardly from a central portion of said main eyeglasses part;
   said clipping means being selectively directly engageable with said elongated member of said clip part so as to pivotably support said eyeglasses part from said clip part such that said main eyeglasses part is pivotably and movable between an operative position wherein said eyeglasses part shields the eyes of a user and an inoperative position wherein said main eyeglasses part extends substantially parallel with said cap visor;
   said elongated member of said clip part being substantially straight and having a substantially rectangular cross section;

said clipping means comprising a central finger and a pair of side fingers, said side fingers being disposed on respective sides of said central finger and extending in oppositely facing relation thereto;

said clipping means being hingedly engageable with said elongated straight member of said clip part such that said central finger engages said straight member on a side thereof opposite to a side of said straight member engaged by said side fingers;

a pair of spaced apart ridge portions being formed around the periphery of said straight member of said clip part;

said side fingers engaging said straight member of said clip part adjacent respective ones of said spaced apart ridge portions;

said side fingers abutting said ridge portions so as to prevent lateral movement of said main eyeglasses part relative to said clip part; and said fingers of said clipping means frictionally engaging said straight member of said clip part so as to securely retain said main eyeglasses part in either of said operative or inoperative positions, while permitting pivotable movement of said main eyeglasses part between said operative and inoperative positions.

* * * * *